United States Patent [19]

Sonoyama et al.

[11] Patent Number: 4,543,331

[45] Date of Patent: Sep. 24, 1985

[54] FERMENTATIVE OR ENZYMATIC PRODUCTION OF 2-KETO-L-GULONIC ACID

[75] Inventors: Takayasu Sonoyama; Shigeo Yagi; Bunji Kageyama, all of Osaka, Japan

[73] Assignee: Shionogi & Co., Ltd., Osaka, Japan

[21] Appl. No.: 469,780

[22] Filed: Feb. 25, 1983

[30] Foreign Application Priority Data

Mar. 5, 1982 [JP] Japan .................................. 57-35452
Mar. 5, 1982 [JP] Japan .................................. 57-35453
Mar. 5, 1982 [JP] Japan .................................. 57-35454

[51] Int. Cl.$^4$ ............................................. C12P 7/60
[52] U.S. Cl. .................................. 435/138; 435/843; 435/847
[58] Field of Search ......................................... 435/138

[56] References Cited

U.S. PATENT DOCUMENTS

| Re. 30,872 | 2/1982 | Sonoyama | 435/138 |
| 3,922,194 | 11/1975 | Sonoyama | 435/138 |
| 3,959,076 | 5/1976 | Sonoyama | 435/138 |
| 3,963,574 | 6/1976 | Sonoyama | 435/138 |
| 3,998,697 | 12/1976 | Sonoyama | 435/138 |

*Primary Examiner*—Sidney Marantz
*Attorney, Agent, or Firm*—Birch, Stewart, Kolasch & Birch

[57] ABSTRACT

Fermentative or enzymatic production of 2-keto-L-gulonic acid from 2,5-diketo-D-gluconic acid using living or processed mutants, being defective in metabolizing 5-keto-D-gluconic acid and incapable of producing 2-keto-D-gluconic acid. The mutant is derived from 2-keto-L-gluconic acid producing microorganisms of genus Corynebacterium. The production is carried out in the presence of nitrates and/or hydrogen donors in a preliminarily sterilized fermentation broth in which a 2,5-diketo-D-gluconic acid producing microorganism of genus Gluconobacter or Erwinia has been cultivated.

24 Claims, No Drawings

FERMENTATIVE OR ENZYMATIC PRODUCTION OF 2-KETO-L-GULONIC ACID

BACKGROUND AND FIELD OF THE INVENTION

The present invention generally relates to the production of 2-keto-L-gulonic acid by microbial (fermentative or enzymatic) reduction of 2,5-diketo-D-gluconic acid. Particularly, it is concerned with (i) use of a newly induced mutant defective in metabolizing 5-keto-D-gluconic acid or its processed product in the reduction process, (ii) the mutant itself, used in performing the process, (iii) addition of a nitrate salt and a hydrogen donor to the reduction system, and (iv) sterilization with a surfactant of a fermentation broth in which a 2,5-diketo-D-gluconic acid producing microorganism has been cultured and which is used as the raw material to be reduced by the mutant or its processed product.

DESCRIPTION OF THE PRIOR ART

The present inventors had previously found various microorganisms capable of producing 2-keto-L-gulonic acid from 2,5-diketo-D-gluconic acid (hereinafter, referred to as 2-keto-L-gulonic acid producing strain (I)), and invented processes for preparing 2-keto-L-gulonic acid by means of the microorganisms (See, for instance U.S. Pat. Nos. 3,922,194 (Re. 30,872), 3,959,076 and 3,963,574). Each of these strains (I) produces 2-keto-D-gluconic acid as an undesired by-product from 2,5-diketo-D-gluconic acid as well as the main product, 2-keto-L-gulonic acid. They had also invented a mixed culture process in order to prevent the accumulation of this undesired 2-keto-D-gluconic acid in the medium (See, for instance, U.S. Pat. No. 3,998,697).

Nevertheless, the establishment of a more commercially feasible process for preparing 2-keto-L-gulonic acid has long been desired. An improvement in the 2-keto-L-gulonic acid production and in its molar yield from the 2,5-diketo-D-gluconic acid has also been awaited to be made.

SUMMARY OF THE INVENTION

It is therefore an object of the present invention to provide an improved microbial process for preparing 2-keto-L-gulonic acid from 2,5-diketo-D-gluconic acid, wherein a newly induced mutant is employed in order to minimize the accumulation of the undesired 2-keto-D-gluconic acid in the fermentation broth, and to provide the a mutant which can be employed in performing said process.

Another object of the present invention is to improve said process, wherein a nitrate salt and a hydrogen donor are added to the fermentation medium for the mutant and/or to the 2,5-diketo-D-gluconic acid to be fed to the medium as the starting material of the process.

A further object of the present invention is to further improve said process, wherein a 2,5-diketo-D-gluconic acid fermentation broth is used as the starting material of the process and the broth is preliminarily sterilized with a surfactant to reduce the number of cells of 2,5-diketo-D-gluconic acid producing microorganism surviving in said broth to a reasonable extent.

According to the present invention, there is provided an improvement in the process for preparing 2-keto-L-gulonic acid from 2,5-diketo-D-gluconic acid in the presence of a living or processed microorganism capable of producing 2-keto-L-gulonic acid. The improvement comprises use of, as said microorganism, a mutant (1) substantially defective in metabolizing 5-keto-D-gluconic acid and (2) substantially incapable of producing 2-keto-D-gluconic acid. The mutant itself employed in performing said process is also provided.

Throughout this specification and claims, the term "living or processed microorganism" means to include any processed product obtained by treating cells of the microorganism as well as the growing or resting ones. The processed product may be exemplified as cell suspension, cell extract, crude or purified enzyme or cell mash obtained from the microorganism. All of the acids participating in the process should be construed to include any of their salts or esters.

According to an aspect of the present invention, there is provided a further improved process wherein the growth of said mutant and the conversion of 2,5-diketo-D-gluconic acid into 2-keto-L-gulonic acid are effected in the presence of a hydrogen donor or a nitrate salt. The hydrogen donor may be added together with the 2,5-diketo-D-gluconic acid to be fed to the medium, or separately to the medium. The nitrate may be added to the medium at the beginning of the cultivation and/or the medium at the start or any time during the 2,5-diketo-D-gluconic acid feeding.

According to another aspect of the present invention, there is provided a still further improvement wherein a fermentation broth, in which a 2,5-diketo-D-gluconic acid producing microorganism (III) has been cultivated, is used as acid 2,5-diketo-D-gluconic acid to be fed to the medium, and viable cells of the microorganism (III) surviving in said broth are sterilized with a surfactant before the feeding.

(1) Derivation of the mutant (II)

The present inventors have now obtained a mutant (II) derived from a parent microorganism strain capable of producing 2-keto-L-gulonic acid from 2,5-diketo-D-gluconic acid (parent strain (I)) by treating the parent strain (I) in a conventional manner for mutation. This mutant (II) is selected so as to never or scarcely grow on 5-keto-D-gluconic acid but to grow on D-gluconic acid and found to be incapable of producing 2-keto-D-gluconic acid. Therefore, it is defined here and will later be referred to as "a mutant substantially defective in metabolizing 5-keto-D-gluconic acid and substantially incapable of producing 2-keto-D-gluconic acid". Namely, when the mutant (II) is contacted with 2,5-diketo-D-gluconic acid under cultivating conditions, 2-keto-L-gulonic acid is produced and accumulated in a contacting mixture without substantial concomitant accumulation of the undesired 2-keto-D-gluconic acid.

Any conventional means for mutation can be employed in order to obtain the mutant (II) from (I) efficiently. The means include exposure to ultraviolet ray radiation or X-ray radiation and treatment with a mutagen such as N-methyl-N'-nitro-N-nitrosoguanidine (N.T.G.), acriflavine, ethyl methanesulfonate and the like.

In an embodiment of the present invention, a suspension of the treated strain (I) is first diluted with sterilized physiological saline to a suitable concentration after optional subsequent incubation, and a portion (0.5–1 ml) of the diluted suspension is spread on a minimum (agar) medium containing 0.5–2% of D-gluconic acid (also containing vitamins and trace elements essential for the growth of microorganism) to grow thereon. Colonies grown on the medium are transferred onto another minimum (agar) medium containing 0.5–2% of 5-keto-D-gluconic acid by the replica plating method, and then colonies which are unable to grow with 5-keto-D-gluconic acid are selected. The cells in the selected colonies completely lack the ability to utilize 5-keto-D-gluconic acid which had been held by the parent strain (I), or the ability is reduced to less than 1/10 as compared with that of the parent strain (I).

It is further confirmed that each of the mutant (II) produces 2-keto-L-gulonic acid without substantial by-production of 2-keto-D-gluconic acid under cultivating conditions in the presence of 2,5-diketo-D-gluconic acid.

The mutant (II) obtained in the above described manner can be exemplified as a mutant FERM-BP 108 derived from a parent strain (I), *Corynebacterium* sp., FERM-P 2770, ATCC No. 31,090, a mutant FERM-BP 107 derived from another (I), *Corynebacterium* sp., FERM-P 2687, ATCC No, 31,081 and the like (Table 1). Detailed taxonomical descriptions of these parent strains (I) are given in any of U.S. Pat. Nos. 3,959,076 and 2,998,697.

TABLE 1

| (2-Keto-L-gulonic acid producing microorganisms (Parents) as contrasted with mutants substantially defective in metabolizing 5-keto-D-gluconic acid and substantially incapable of producing 2-keto-D-gluconic acid (Mutants), derived from the former) | |
|---|---|
| Parents | Mutants |
| Corynebacterium sp. FERM-P 2770, ATCC No. 31,090 | FERM-BP 108 |
| Corynebacterium sp. FERM-P 2687, ATCC No. 31,081 | FERM-BP 107 |

The above described fact that the deletion or remarkable decrease in 2-keto-D-gluconic acid producing activity is brought about by the deletion of 5-keto-D-gluconic acid metabolic activity from the parent strain is common to every 2-keto-L-gulonic acid producing microorganism which belong to Coryneform Group of Bacteria (according to the definition given in Bergey's Manual of Determinative Bacteriology 8th Ed.). Any further mutants or variants of said mutant (II) may also be employed in embodying the disclosed process as far as they possess this property. Furthermore, any microorganisms being introduced with the gene expressing this character of the mutant (II) prepared by gene-cloning, transformation or cell fusion may also be employed.

(2) Conversion of 2,5-diketo-D-gluconic acid into 2-keto-L-gulonic acid in the presence of the mutant (II)

Any of the known conventional conditions employed in cultivating a parent strain (I), treating the cultured broth and recovering 2-keto-L-gulonic acid from the broth, as disclosed in, for instance, U.S. Pat. Nos. 3,922,194, 3,959,076 and 3,963,574, may likewise be applied to the cultivation of the mutant (II) and its subsequent steps, with some obvious modifications.

No particular restriction should be imposed on the composition of medium used for cultivating the mutant (II). For instance, sugars such as glucose, fructose, sucrose and molasses and polyhydric alcohols such as glycerol may be used as the carbon source in a concentration of 0.5–5%, and conventional nitrogen containing substances such as corn steep liquor, peptone, meat extract, ammoniums, nitrates and the like may be used as the nitrogen source in a concentration of 0.5–5%. Other inorganic salts (for example, salts of calcium, magnesium, potassium, zinc, manganese and iron) or any factor capable of promoting the production of the end product may be added to the composition. The composition may vary with the property of the strain employed, the amount of the raw material, 2,5-diketo-D-gluconic acid and the other attendant conditions.

An aqueous solution of any salts of 2,5-diketo-D-gluconic acid may be used as the raw material. Alternatively, it is also appropriate to use a fermentation broth obtained by cultivating a microorganism capable of producing 2,5-diketo-D-gluconic acid from D-glucose which may belong to genus Erwinia or genus Gluconobacter (according to the definition given in Bergey's Manual of Determinative Bacteriology 8th Ed. and therefore includes genera Acetomonas, Acetobacter and Gluconobacter in that of 7th Ed.) as a filtrate free from cells or a solution sterilized with chemicals (for example, sodium dodecyl sulfonate).

The 2,5-diketo-D-gluconic acid producing microorganism (III) employed in embodying the process of the present invention is a microorganism which belongs to genus Gluconobacter or genus Erwinia and can be exemplified as indicated in Table 2 below.

TABLE 2

| Microorganism | FERM-P | ATCC |
|---|---|---|
| *Acetomonas albosesamea* | 2439 | 21998 |
| *Gluconobacter melanogenum* IFO 3293 | — | — |
| *Gluconobacter rubisinosus* IFO 3244 | — | — |
| *Erwinia citreus* | 5449 | 31623 |
| *Erwinia punctata* | 5452 | 31626 |
| *Erwinia punctata* var. | 5450 | 31624 |
| *Erwinia punctata* var. | 5451 | 31625 |
| *Erwinia punctata* var. | 5453 | 31627 |
| *Erwinia terreus* | 5454 | 31628 |
| *Erwinia terreus* var. | 5455 | 31629 |
| *Erwinia terreus* var. | 5456 | 31630 |
| *Erwinia terreus* var. | 5457 | 31631 |

Detailed taxonomical descriptions of these strains are given in either of U.S. Pat. No. 3,998,697 or European Patent Publication No. 0 046 284.

Samples of these microorganism strains as well as those described previously have been deposited with Fermentation Research Institute, Yatabe, Japan and/or American Type Culture Collection, Maryland, U.S.A. and are available from these depositories under the provision of Budapest Treaty. Microorganisms identified with an IFO number are also available from Institute of Fermentation, Osaka, Japan.

Although the amount of 2,5-diketo-D-gluconic acid to be fed to the medium and its manner of feeding vary with the microorganisms employed and the conditions of the medium and cultivation, said acid is usually added at once or by portions intermittently (feeding) to give an overall concentration of 1–10% to the medium or cultured broth. The amount of said acid in each portionwise addition is preferably adjusted to give 0.05–2% in concentration with respect to the total amount of the medium or cultured broth at the time of the feeding.

The pH of the medium or cultured broth may usually be maintained at 5.0–9.0, and preferably at 6.0–8.5 during the conversion by occasional addition of alkaline substance, for instance, calcium carbonate. Alternatively, any suitable buffer may be added to the medium at the beginning of the cultivation.

These conditions are applicable to other embodiments of the present invention in the subsequent description with some modification.

Of the investigated surfactants, sodium dodecyl sulfate (SDS) is found to be particularly preferable.

The process of the present invention will briefly be demonstrated as follows.

At first, a medium containing the substrate, D-glucose, nitrogen source such as corn steep liquor and inorganic salt is inoculated with the 2,5-diketo-D-gluconic acid-producing strain (III), and cultured at 28° C. with agitation and aeration.

Next, the fermentation broth prepared as described above is divided into two portions and one is treated by aseptically adding one of the surfactants to give its final concentration of 0.01–0.25 w/v % and is allowed to stand at 5°–28° C. for several hours with occasional and moderate agitation. Another portion without addition of the surfactant is likewise kept at 5°–28° C. for several hours.

During the surfactant treatment which uses, for instance, sodium dodecyl sulfate (SDS), the number of viable cells of the strain (III) in the treated broth decreases to less than one millionth of that of the untreated broth. The decrease may however vary with the strains and surfactant employed. Another portion of the untreated 2,5-diketo-D-gluconic acid fermentation broth is sterilized by filtration.

Then D-glucose as hydrogen donor is aseptically added to each of the surfactant-treated broth, the broth sterilized by filtration and the untreated 2,5-diketo-D-gluconic acid fermentation broth, respectively, to give its final concentration of 1–10%, before the broths are fed to the culture of the mutant (II).

Apart from this, the mutant (II) is timely cultured at the time of the surfactant treatment of the 2,5-diketo-D-gluconic acid fermentation broth. To the culture of the mutant (II), each of the previously prepared three 2,5-diketo-D-gluconic acid fermentation broths is fed by portions at every 15–120 min. to give its 2,5-diketo-D-gluconic acid concentration of 0.05–2.0% while monitoring the amount of 2,5-diketo-D-gluconic acid remaining in the broth, and the cultivation is continued for 48 hours after the beginning of the feeding. In either the case of sterilization by the surfactant treatment or by filtration, 2,5-diketo-D-gluconic acid is smoothly converted into 2-keto-L-gulonic acid. Nevertheless, in the case of no sterilization, the cell population of the strain (III) reaches more than $10^5$ cells/ml to finally stop the production of 2-keto-L-gulonic acid.

As will be demonstrated later in the Examples, the sterilization may be achieved by treatment with surfactant or by filtration. But, since the sterilization by filtration of the broth is, however, possible only in a bench scale treatment if the broth contains 2,5-diketo-D-gluconic acid in a high concentration and is considered to be almost impossible to embody it in a commercial scale production in view of its expensiveness. Therefore, the sterilization with surfactant according to this aspect of the present invention is proved to be of great advantage.

DESCRIPTION OF THE PREFERRED EMBODIMENTS

In the following description, the present invention will be elucidated in more detail by way of example. The contents and order of the description is as follows:
Example 1. Derivation of the mutant (II).
Preparation A. 2,5-Diketo-D-gluconic acid fermentation broth.
Preparation B. Solution of Ca 2,5-diketo-D-gluconate.
Example 2. Use of the mutant (II) in 2-keto-L-gulonic acod production by fermentation.
Example 3. Use of cell suspension and cell extract of the mutant (II) in 2-keto-L-gulonic acid production by contacting.
Example 4. Addition of a nitrate salt and a hydrogen donor to the fermentation broth.
Example 5. Sterilization of 2,5-diketo-D-gluconic acid fermentation broth with surfactant.

Method of analysis (i) 2-Keto-L-gulonic acid, 2-keto-D-gluconic acid and 2.5-diketo-D-gluconic acid (a) Gas-liquid chromatography:
Column: SE 52 (5%); Sample: Trimethylsilylated; Carrier gas: Helium; Temperature; 160°–210° C.
(b) Paper or thin-layer chromatography:
Carrier: Toyo Roshi No. 50 or TLC aluminum sheet cellulose (available from Toyo Roshi K.K. or Merck A.G.)
Developing solvent: Phenol:formic acid:water=75:4:25
Color development: Spraying AHF solution (prepared by dissolving 0.93 g of aniline and 1.66 g of phthalic acid in 100 ml of water-saturated n-butanol) and heating at 105° C. for 2 minutes.

(ii) D-glucose

"Glucose B test" available from Wako Junyaku Kogyo K.K.

EXAMPLE 1 (Derivation of the mutant (II))

(1) Liquid mediumm

An aqueous solution containing:

| Bacto Beef Extract (Difco) | 1.0% |
|---|---|
| Bacto Peptone (Difco) | 1.0% and |
| NaCl | 0.5% | was adjusted to pH 7.2. Each 50 ml portions was placed in a 500 ml conical flask and sterilized at 115° C. for 20 minutes.

(2) Minimum(agar)medium

A medium of the following composition was adjusted to pH 7.2 and sterilized at 115° C. for 15 minutes.

| $NH_4Cl$ | 0.5% |
|---|---|
| $NH_4NO_3$ | 0.1% |
| $Na_2SO_4$ | 0.2% |
| $MgSO_4.7H_2O$ | 0.1% |
| $CaCO_3$ | 0.0001% |
| $KH_2PO_4$ | 0.3% |
| $K_2HPO_4$ | 0.1% |
| Trace element solution* | 0.1% |
| Vitamin solution** | 0.1% and |
| Agar | 2.0% |
| $Na_2B_4O_7.10H_2O$ | 88 mg |
| $(NH_4)_6Mo_7O_{24}.4H_2O$ | 37 mg |
| $FeCl_3.6H_2O$ | 970 mg |
| $ZnSO_4.7H_2O$ | 88 mg |
| $CuSO_4.5H_2O$ | 270 mg and |
| $MnCl_2.4H_2O$ | 27 mg |
| Thiamine | 1.0 mg |
| Pantothenic acid | 10 mg |
| Niacin | 10 mg and |
| Biotin | 0.1 mg |

*Trace element solution (ingredients per liter)
**Vitamin solution (ingredients per liter)

(3) Use of nitrate salt and hydrogen donor in the cultivation

In the course of embodying the process for preparing 2-keto-L-gulonic acid from 2,5-diketo-D-gluconic acid without concomitant accumulation of 2-keto-D-gluconic acid by employing the mutant (II), the present inventors have now found that the production of 2-keto-L-gulonic acid can remarkably be increased and the molar yield of 2-keto-L-gulonic acid from 2,5-diketo-D-gluconic acid can also remarkably be improved by adding a nitrate to the broth for the growth of mutant (II) and/or to a medium wherein the mutant (II) acts on 2,5-diketo-D-gluconic acid, and by adding a hydrogen donor to the broth simultaneously with the addition of 2,5-diketo-D-gluconic acid, and they have completed the second aspect of the present invention based on these findings.

When the mutant (II) is inoculated and incubated in such a medium supplemented with 0.1–0.5% of nitrates, the growth of the mutant (II) reaches its maximum in 10–24 hours after the beginning of the incubation. Furthermore, the nitrate is added to the medium in a concentration of 0.05–0.5% at a phase wherein the growth reaches its maximum or within 10 hours after this phase. The nitrates which can be employed in this process include alkali metal salts such as potassium nitrate and sodium nitrate, alkaline earth metal salts such as calcium nitrate and magnesium nitrate, and manganese nitrate.

The nitrate may be added to the medium at the beginning of the cultivation of the mutant (II). The addition may also be effected simultaneously with the feeding of 2,5-diketo-D-gluconic acid all at once, or by portions subsequent to the feeding. Desirably, it may be effected at the beginning of the cultivation and at the start of 2,5-diketo-D-gluconic acid feeding. It is also found that the advantage attributable to the addition of the nitrate becomes more remarkable by the addition of a hydrogen donor to the medium simultaneously with the 2,5-diketo-D-gluconic acid feeding. Namely, the production of 2-keto-L-gulonic acid can also be remarkably increased by the addition of a hydrogen donor.

As the hydrogen donor, any carbohydrates and polyhydric alcohols may be employed as far as the strain can utilize them. It is desirable to add the hydrogen donor simultaneously with the feeding of 2,5-diketo-D-gluconic acid in combination with the 2,5-diketo-D-gluconic acid. Although the concentration of the hydrogen donor may vary with the conditions of adding 2,5-diketo-D-gluconic acid and of the mutant to be employed or the broth in which the mutant had been incubated, the hydrogen donor is usually added in a concentration ranging from 5% to 50% of the amount of the 2,5-diketo-D-gluconic acid to be fed.

The advantage by the addition of the nitrate according to the present invention is attributable to the fact that the nitrate participates in the metabolism of the carbohydrate or organic acid added as the hydrogen donor by the microorganism cells. It also activates a reduction system of 2,5-diketo-D-gluconic acid into 2-keto-L-gulonic acid in the microorganism cells and plays a roll of conferring hydrogen liberated from the hydrogen donor to the reduction system efficiently. Without this addition of the hydrogen donor, the effect of the sole addition of the nitrate would be of little value on the production of 2-keto-L-gulonic acid; i.e., the advantage of the nitrate salt addition on the increase in the production and high yield of 2-keto-L-gulonic acid could remarkably be improved by the very addition of the hydrogen donor.

In addition to the above-described advantages, the nitrate addition is also effective in prolonged maintenance of the prefixed pH value (6.5–8.0) of the broth, which is preferred for the production of 2-keto-L-gulonic acid from 2,5-diketo-D-gluconic acid.

It is presumed that the nitrate serves to improve the metabolism of hydrogen donor by the microorganism and contributes to the activation and stabilization of the reduction system rather than its utilization by the microorganism as a nitrogen source.

In general, the effect of a nitrogen containing compound as the utilizable nitrogen source is evaluated in terms of the increase in the cell concentration. Among similar inorganic compounds, an ammonium salt has a much larger effect on this increase than the nitrate has. Namely, the ammonium salt is effective for the increase in the cell concentration when it is added to the broth at the beginning of the cultivation or at the time of 2,5-diketo-D-gluconic acid feeding but has only small effect on the increased 2-keto-L-gulonic acid production.

In contrast to this, the nitrate has a smaller effect on the increase of the cell concentration than the ammonium salt has but contributes to the remarkable increase in the 2-keto-L-gulonic acid production. These effects will later be demonstrated in Example.

(4) Sterilization of 2,5-diketo-D-gluconic acid fermentation broth with surfactant In the further course of embodying a commercial production of 2-keto-L-gulonic acid, the present inventors have attempted to effectively produce 2-keto-L-gulonic acid by feeding directly the 2,5-diketo-D-gluconic acid fermentation broth prepared by cultivating the strain (III) (containing, $10^8$–$10^{10}$ viable cells of (III)/ml to the cultured broth of the mutant (II)).

In the attempted process, it has been found that, different from the case of the parent strain (I), when the mutant (II) is employed in the above process, the production of 2-keto-L-gulonic acid is remarkably inhibited. As a result of extensive investigation, it has been made clear that the inhibitory phenomenon occurs in a case wherein the strain (III) is grown above $10^5$ viable cells/ml in the process.

As a means for sterilizing the strain (III) in the 2,5-diketo-D-gluconic acid fermentation broth, a thermal sterilization and a sterlization by filtration are envisioned. However, because of the thermal instability of 2,5-diketo-D-gluconic acid and of high cost with poor practical feasibility in a commercial scale production of the sterilization by filtration, an establishment of an alternative means for sterilization of the strain (III) has been found to be indispensible for embodying the commercial production of 2-keto-L-gulonic acid by the present inventors. After a series of diversified study, the third aspect of the present invention has been completed by establishing a safe and sure means for sterilizing the string (III) with a surfactant.

This aspect of the present invention has advantages in that no additional facility especially designed for the sterilization is required in embodying the process, the surfactant can easily be singled out from the many so that it will not inhibit the production of 2-keto-L-gulonic acid by the mutant (II), and the surfactant itself is inexpensive and easily available.

An attendant advantage is that the process can easily be embodied in a large-scale production.

(v) End point

The fermentation was terminated at a time when the pink spot of 2-keto-D-gluconic acid disappeared from a thin-layer chromatogram of the broth.

PREPARATION B (Solution of calcium 2,5-diketo-D-gluconate)

An aqueous solution containing 5% powdery calcium 2,5-diketo-gluconate in concentration of 5.0% was sterilized by filtration.

EXAMPLE 2 (Use of the mutant (II) in 2-keto-L-gulonic acid production by fermentation)

seed culture was inoculated in the fermentation medium (2) and cultured. Either one of solutions of 2,5-diketo-D-gluconic acid (Preparations A and B) was added to this fermentation medium to give a final concentration of 2%, at the beginning or at any time within 16 hours after the beginning of the fermentation and the fermentation was continued for further 48 hours.

The results of the gas-liquid chromatogrphy of the products are summarized in Table 4 below. As indicated in Table 4, no 2-keto-D-gluconic acid was detected from the broths of the mutant (II) whereas a considerable amount of said acid was detected from those of the parent (I).

TABLE 4

Accumulations (mg/ml) of 2-keto-L-gulonic acid and 2-keto-D-gluconic acid in broths, in which each of the parent strains (I) and each of the mutants (II) was cultured, determined at the 48th hour after the beginning of the cultivations.

| 2-Keto-L-gulonic acid producing microorganism strains | Time of feeding 2,5-diketo-D-gluconic acid, hours after the beginning of cultivation. | Aqueous solution of calcium 2,5-diketo-D-gluconate (sterilized by filtration) | | Broth of FERM-P 5452, ATCC 31626 (Sterilized by filtration) | |
|---|---|---|---|---|---|
| | | 2KLG, mg/ml | 2KDG, mg/ml | 2KLG, mg/ml | 2KDG, mg/ml |
| Corynebacterium sp. FERM-P 2770, ATCC No. 31090 | 0 | 1.50 | 0.46 | 1.75 | 0.58 |
| | 16 | 3.85 | 1.38 | 4.10 | 1.45 |
| 5-Keto-D-gluconic acid metabolism deficient mutant (FERM-BP 108) | 0 | 5.20 | 0 | 5.33 | 0 |
| | 16 | 7.30 | 0 | 8.20 | 0 |
| Corynebacterium sp. FERM-P 2687, ATCC No. 31081 | 0 | 0.28 | 0.42 | 0.38 | 0.24 |
| | 16 | 0.70 | 0.70 | 0.73 | 0.68 |
| 5-Keto-D-gluconic acid metabolism deficient mutant (FERM-BP 107) | 0 | 0.25 | 0 | 0.40 | 0 |
| | 16 | 0.83 | 0 | 0.86 | 0 |

2KLG: 2-keto-L-gulonic acid,
2KDG: 2-keto-D-gluconic acid (1) Seed medium (Common to the subsequent examples)

An aqueous solution containing:

| | |
|---|---|
| D-glucose | 1.0% |
| Bacto Yeast extract (Difco) | 0.5 |
| Bacto Peptone (Difco) | 0.5 |
| Potassium primary phosphate (KH$_2$PO$_4$) | 0.1% and |
| Magnesium sulfate (MgSO$_4$.7H$_2$O) | 0.02% | was adjusted to pH 7-7.2 with 10% NaOH solution. Each 50 ml portion was poured into 500 ml conical flask and sterilized at 115° C for 20 minutes.

(2) Fermentation medium

An aqueous solution containing:

| | |
|---|---|
| D-glucose | 1.0% |
| Corn steep Liquor (CSL) | 3.0% |
| KH$_2$PO$_4$ | 0.1% and |
| MgSO$_4$.7H$_2$O | 0.02% | was adjusted to pH 7-7.2 with 10% NaOH.

Each 50 ml portion was placed in 500 ml conical flask and sterilized at 115° C. for 20 minutes.

(3) Preparation of 2-keto-L-gulonic acid

The seed medium (1) was inoculated with one loopful each of the 2-keto-L-gulonic acid-producing microorganism (parent (I)) or mutants (II) derived from (I), shown in Table 4 and the inoculated medium was cultured at 28° C. for 24 hours. Thereafter, each 5 ml of this

EXAMPLE 3 (Uses of cell suspension and cell extract in 2-keto-L-gulonic acid production by contacting)

(1) Seed culture

The seed medium as described in Example 2, (1) was inoculated with each one loopful of Corynebacterium sp. FERM-P 2770 (I) or the mutant defective in metabolizing 5-keto-D-gluconic acid and substantially incapable of producing 2-keto-D-gluconic acid FERM-BP 108 (II), and cultured under agitation at 28° C. for 24 hours.

(2) Culture for preparing cell suspension or extract

The fermentation medium (455 ml) as described in Example 2, (2), further containing 0.01% of antifoam, polypropylene glycol 2000 (P 2000) was aseptically placed in a 1 liter fermenter and inoculated with each 45 ml of the seed culture broth (1). Fermentation was performed at 28° C. for 16 hours with agitation of 1740 r.p.m. and at an air flow rate of 600 Nml/min.

(3) Preparation of cell suspension

The cultured broth (2) was centrifuged (15,000 r.p.m.) to collect cells which were then washed twice with physiological saline. The washed cells were suspended in 0.05M Tris buffer (pH 7.5) to give a suspension of OD$_{660\ nm}$ = 12.

(4) Preparation of cell extract

The cells washed in the same manner as described in (3) above were suspended in 0.05M Tris buffer (pH 7.8) to give a suspension of OD$_{660\ nm}$ = 100, which was passed through a French pressure cell press at 1,000 Kg/cm. The intact cells and cell debris were removed

(3) Solution of D-gluconic acid and of 5-keto-D-gluconic acid

Each of aqueous solutions (10%) of sodium D-gluconate and of sodium 5-keto-D-gluconate was adjusted to pH 6.8–7.2 and sterilized by filtration.

(4) Method for isolation of the mutants

One loopful each of *Corynebacterium* sp. FERM-P 2770 and *Corynebacterium* sp. FERM-P 2687 was inoculated in the liquid medium (1) and cultured at 28° C. for 8 hours. To each of the cultured media, previously sterilized 0.2% aqueous solution of N-methyl-N'-nitro-N-nitroso-guanidine was added to give a final concentration of 0.02% and the incubation was continued for another 30 minutes. The incubated medium was centrifuged (10,000 r.p.m., 15 minutes) and cells were collected therefrom.

The collected cells were washed three times with sterilized physiological saline and suspended in each 10 ml of the saline. Each 1 ml of the suspension was inoculated in the medium (1) and cultured at 28° C. for 15 hours. The culture was then diluted to $10^2$–$10^3$ viable cells per milliliter with sterilized saline. Then, each 0.5–1 ml of the diluted culture was spread over a plate medium prepared by mixing D-gluconic acid solution (3) with the minimum agar medium (2) in the proportion of 1 to 9 and allowed to grow at 28° C. for 3–5 days.

Colonies of the grown cells (strain (1) of Table 3 which grow in D-gluconic acid medium) were transferred with a velveteen cloth to a plate medium prepared by mixing 5-keto-D-gluconic acid solution (3) with the minimum agar medium (2) in the proportion of 1 to 9. After being incubated for 3–5 days, colonies of the cells that grew on the D-gluconic acid medium but did not grow on the 5-keto-D-gluconic acid medium were picked up and inoculated to be incubated in the D-gluconic acid medium.

The thus selected mutant (strain (2) in Table 3 which cannot grow on the 5-keto-D-gluconic acid medium) was inoculated in the medium (1) containing 1% of 5-keto-D-gluconic acid and cultured at 28° C. for 24 hours. 5-Keto-D-gluconic acid remaining in the culture was determined by means of paper chromatography in order to confirm that this strain (2) was unable to utilize 5-keto-D-gluconic acid.

The medium (2) which will be described in Example 2 was inoculated with one loopful of the mutant confirmed to be unable to utilize 5-keto-D-gluconic acid (Strain (3) in Table 3) and incubated for 20 hours. To this incubated medium, was added the calcium 2,5-diketo-D-gluconate solution which will be described in Preparation B to give a final concentration of 1.0% and the incubation continued for further 24 hours.

The amounts of 2-keto-D-gluconic acid and 2-keto-L-gulonic acid in the cultured medium were determined by means of paper chromatography. The results are shown in Table 3 below.

Thus, 308 desired mutants defective in metabolizing 5-keto-D-gluconic acid and substantially incapable of producing 2-keto-D-gluconic acid were obtained from 84,520 colonies of mutagenized *Corynebacterium* sp. FERM-P 2770 to grow out, and in a similar manner, 11 desired mutants were obtained from 29,100 colonies of mutagenized *Corynebacterium* sp. FERM-P 2687.

TABLE 3

| 2-Keto-L-gulonic acid producing microorganism (parents) | Corynebacterium sp. FERM-P 2770 | Corynebacterium sp. FERM-P 2687 |
|---|---|---|
| | (Number of the mutant strains) | |
| Strains (1) which can grow on D-gluconic acid medium | 84,520 | 29,100 |
| Strains (2) of those (1) which cannot grow on 5-keto-D-gluconic acid medium | 363 | 45 |
| Strains (3) of those (1) which cannot utilize 5-keto-D-gluconic acid | 319 | 13 |
| Strains of those (3) which produce 2-keto-L-gulonic acid but do not produce 2-keto-D-gluconic acid | 308 | 11 |

PREPARATION A (2,5-Diketo-D-gluconic acid fermentation broth.)

(i) Seed medium

An aqueous solution containing:

| | |
|---|---|
| D-glucose | 1.0% |
| Corn steep liquor (CSL) | 5.0% |
| Potassium primary phosphate ($KH_2PO_4$) | 0.1% |
| Magnesium sulfate ($MgSO_4.7H_2O$) | 0.02% and |
| Calcium carbonate ($CaCO_3$) | 0.5% | was adjusted to pH 6.8–7.0 with 10% NaOH solution and divided into 50 ml portions to be placed in a 500 ml conical flask, respectively. The seed medium was sterilized at 120° C. for 20 minutes.

(ii) Seed culture

The seed medium (i) in the flask was inoculated with one loopful of *Erwinia punctata* FERM-P 5452 shown in Table 1 and incubated under agitation (71 mm in amplitude, 270 r.p.m.) at 28° C. for 8–11 hours. The seed culture was terminated at a time point when its optical density reached about 8 (end point).

(iii) Fermentation medium

An aqueous solution containing:

| | |
|---|---|
| D-glucose | 20% |
| CSL | 3% |
| $KH_2PO_4$ | 0.1% |
| $CaCO_3$ | 6.3% and |
| Antifoam, polypropylene glycol (P-2000) | 0.01% | was adjusted to pH 6.8–7.0, sterilized at 120° C. for 20 minutes, and each 455 ml portion was poured aseptically into a sterilized 1 liter fermenter and, each 45 ml of the above seed culture (ii) was added.

(iv) Fermentation

A fermentation was carried out at 28° C. with air flow rate of 600 Nml/minutes and agitation at 1740 r.p.m. for 20–30 hours (final 2,5-diketo-D-gluconic acid concentration being about 19 w/v %). The broth was centrifuged to remove the cells and the supernatant thereof was sterilized by filtration. This was used as the 2,5-diketo-D-gluconic acid fermentation broth.

by centrifugation at 20,000 G for 30 min. The resultant supernatant thereof was dialyzed against 0.05M Tris buffer (pH 7.5) for 15 hours and defined as a cell extract.

(5) Production 2-keto-L-gulonic acid with the cell suspension (3)

Eight (8) ml of the cell suspension (3) was combined with 2 ml of Ca 2,5-diketo-D-gluconate solution (Preparation B) and the mixture was allowed to react at 30° C. for 15 hours with shaking. Thereafter, the reaction mixture was centrifuged (15,000 G, 15 min.) to remove the cells and analyzed for 2-keto-L-gulonic acid and 2-keto-D-gluconic acid by gas-liquid chromatography. The results of the quantitative determination are given in Table 5 below.

TABLE 5

| Microorganisms used for preparing the cell suspention: | Concentration in the reaction mixture: | |
| --- | --- | --- |
| | 2-keto-L-gulonic acid | 2-keto-D-gluconic acid |
| Corynebacterium sp. FERM-P 2770 ATCC 31090 | 1.93 mg/ml | 0.64 mg/ml |
| Mutant defective in metabolizing 5-keto-D-gluconic acid FERM-BP 108 | 2.65 mg/ml | 0 mg/ml |

(6) Production of 2-keto-L-gulonic acid with the cell extract (4)

The cell extract (4)(0.5 ml) was added to 2.5 ml of 0.1M Tris buffer (pH 7.5) containing 75μ moles of Ca 2,5-diketo-D-gluconate and 15μ moles of NADPH (Reduced nicotinamide adenine dinucleotide phosphate) to be allowed to react at 30° C. for 16 hours. The results of quantitative determination of the reaction mixture are given in Table 6 below.

TABLE 6

| Microorganisms used for preparing the cell extract: | Concentration in the reaction mixture: | |
| --- | --- | --- |
| | 2-keto-L-gulonic acid | 2-keto-D-gluconic acid |
| Corynebacterium sp. FERM-P 2770 ATCC 31090 | 285 mcg/ml | 32 mcg/ml |
| Mutant defective in metabolizing 5-keto-D-gluconic acid FERM-BP 108 | 356 mcg/ml | 0 mcg/ml |

From the results shown in Tables 5 and 6 above, it was confirmed that 2-keto-L-gulonic acid was produced in either of the reactions wherein the cell suspension (3) or cell extract (4) was used.

In both cases, the products, prepared from the parent 2-keto-L-gulonic acid producing microorganism strain, FERM-P 2770 (I), however produce 2-keto-D-gluconic acid together with 2-keto-L-gulonic acid, while those prepared from the mutant (II) produce 2-keto-L-gulonic acid but do not produce 2-keto-D-gluconic acid.

EXAMPLE 4 (ADDITION OF A NITRATE AND A HYDROGEN DONOR TO THE FERMENTATION BROTH)

(1) 2,5-Diketo-D-gluconic acid fermentation broth

The fermentation broth prepared in accordance with Preparation A was centrifuged (10,000 r.p.m., 15 minutes) to remove cells and its supernatant was sterilized by filtration (2,5-diketo-D-gluconic acid concentration: 19%).

The sterilized fermentation broth was mixed with a sterilized aqueous D-glucose solution (50%) to give a final concentration of 3.8% of the hydrogen donor, D-glucose to the broth.

(2) Fermentation medium (common to the subsequent Examples for the preparation of 2-keto-L-gulonic acid)

An aqueous solution containing:

| D-glucose | 2.0% |
| --- | --- |
| CSL | 3.0% |
| KH$_2$PO | 0.1% |
| MgSO$_4$.7H$_2$O | 0.02% and |
| Antifoam: polypropylene glycol (P-2000) | 0.01% | was adjusted to pH 7.0–7.2 and each 450 ml portion was sterilized at 115° C. for 20 minutes and aseptically placed in a sterilized 1 liter fermenter.

(3) Preparation of nitrogen compound additives

Each of sodium nitrate, potassium nitrate, sodium nitrite and ammonium chloride was individually dissolved in water to make each 10% aqueous solution to be sterilized by filtration, to give the additives for the media at the beginning of culture and of the start of 2,5-diketo-D-gluconic acid feeding.

(4) Fermentation (for the preparation of 2-keto-L-gulonic acid)

The seed medium as described in Example 2, (1), was inoculated with one loopful of a mutant defective in metabolizing 5-keto-D-gluconic acid and substantially incapable of producing 2-keto-D-gluconic acid, FERM-BP 108 derived from Corynebacterium sp. FERM-P 2770, ATCC No. 31090 and the inoculated medium was incubated with shaking at 28° C. for 20–24 hours. Each 50 ml of this seed culture was inoculated in the fermentation medium (2) and, after being aseptically added with the various nitrogen compound additives prepared in accordance with the above (3) to give a final concentration of 0.25%, it was cultivated at 28° C. at an air flow rate of 1.2 v.v.m. and 1740 r.p.m. for 10–16 hours.

After confirmation of the disappearance of D-glucose by the quantitative determination described above, each of the nitrogen compound additives (3) was added again to give a final concentration of 0.1%. Furthermore, the 2,5-diketo-D-gluconic acid fermentation broth containing 3.8% of D-glucose was added to make the latter's final concentration 0.2%.

Subsequently, 2,5-diketo-D-gluconic acid was fed by portions to the culture every 15–120 minutes to give a concentration about 0.2% just after each feeding while monitoring elimination of said acid from the broth.

The 2,5-diketo-D-gluconic acid feeding was terminated at the 45th hour after the start of the feeding but the cultivation was continued for further 3 hours (total cultivation time after the start: 48 hours).

After the cultivation is completed, the broth was analyzed for 2-keto-L-gulonic acid, 2-keto-D-gluconic acid and 2,5-diketo-D-gluconic acid, individually by gas chromatography.

As a result, it was confirmed that no 2-keto-D-gluconic acid was detected from either of the media. Accumulations of 2-keto-L-gulonic acid in the broth with various nitrogen compound additives were summarized in Table 7 below.

TABLE 7

Advantages of various nitrogen compound additives on the accumulation of 2-keto-L-gulonic acid to the initial fermentation medium and to the same medium at the start of the 2,5-diketo-D-gluconic acid feeding.

(Figures in Table indicate the accumulation of 2-keto-L-gulonic acid in the medium, and figures in the parenthesis indicate the molar yield of 2-keto-L-gulonic acid from precursor, obtained by the following formula: (2-keto-L-gulonic acid, produced (mol) ÷ (2,5-diketo-D-gluconic acid consumed (mol) × 100)

| Nitrogen compound added to the initial fermentation medium | Presence of hydrogen donor (D-glucose) | Nitrogen compound added at the beginning of the 2,5-diketo-D-Gluconic acid addition 2-keto-L-gulonic acid accumulation, mg/ml, (molar yield of 2-keto-L-gulonic acid, %) | | | | |
|---|---|---|---|---|---|---|
| | | None mg/ml % | Sodium nitrate mg % | Potassium nitrate mg/ml % | Sodium nitrite mg/ml % | Ammonium chloride mg/ml % |
| None | None | 8.2 (41) | 8.9 (43) | 9.0 (43) | 3.9 (38) | 8.9 (46) |
| | Added | 15.7 (75) | 22.0 (87) | 22.1 (86) | 6.0 (62) | 16.0 (78) |
| Sodium nitrate | None | 8.6 (49) | 12.1 (48) | | 4.4 (45) | 9.2 (43) |
| | Added | 26.5 (91) | 40.2 (93) | | 16.0 (88) | 27.5 (90) |
| Potassium nitrate | None | 8.8 (52) | | 12.2 (46) | | |
| | Added | 25.8 (92) | | 40.3 (93) | | |
| Sodium nitrite | None | 3.2 (31) | | | 3.6 (38) | |
| | Added | 8.1 (54) | | | 7.8 (53) | |
| Ammonium chloride | None | 9.2 (42) | | | | 9.7 (45) |
| | Added | 17.0 (78) | | | | 18.3 (80) |

As shown in Table 7 above, in which a comparison is made between a case wherein a nitrate is added to the medium or broth at the beginning of the fermentation as well as at the start of the 2,5-diketo-D-gluconic acid feeding, and D-glucose which serves as the hydrogen donor is added together with the feeding of 2,5-diketo-D-gluconic acid, and another case wherein no such addition is made, it is obvious that the accumulation of 2-keto-L-gulonic acid in the broth increases from 8.2 mg/ml to 40 mg/ml (about five fold increase) and the yield (mol %) of 2-keto-L-gulonic acid increases from 41% to 93%.

On the other hand, the cell concentration in terms of optical density (O.D.) at the time when D-glucose disappear from the broth is measured as summarized in Table 8 below, which indicates that the nitrate is not as effective as the nitrogen nutrient source. As indicated in Table 8, although the increase in the cell concentration by the addition of the nitrate is limited only to 11.6%, the increase by the addition of the ammonium salt reaches about 40%. This fact shows that the effect of the nitrate as the nitrogen source is less than that of the ammonium salt.

From the above fact, it is confirmed that the addition of nitrate to the medium has only a small effect on the increase in the cell concentration, but has a great advantage on the increase in the 2-keto-L-gulonic acid production and on the improvement in molar yield of converting 2,5-diketo-D-gluconic acid into 2-keto-L-gulonic acid.

TABLE 8

Effect of the additives added at the beginning of the cultivation on the growth of the microorganisms (FIG. in Table indicate the cell concentration at the time when D-glucose disappears in terms of optical density (O.D.) measured at 660 nm)

| Additives at the beginning of the cultivation | Optical density (O.D.) |
|---|---|
| None | 13.7 |
| Sodium nitrate | 15.3 |
| Potassium nitrate | 15.0 |

TABLE 8-continued

Effect of the additives added at the beginning of the cultivation on the growth of the microorganisms (FIG. in Table indicate the cell concentration at the time when D-glucose disappears in terms of optical density (O.D.) measured at 660 nm)

| Additives at the beginning of the cultivation | Optical density (O.D.) |
|---|---|
| Sodium nitrite | 11.1 |
| Ammonium chloride | 19.3 |

EXAMPLE 5 (STERILIZATION OF 2,5-DIKETO-D-GLUCONIC ACID FERMENTATION BROTH WITH SURFACTANT)

The broth prepared in accordance with Preparation A was divided into several portions immediately after the culture was terminated. Each of the listed surfactants was aseptically added to each portion of the broth to give a final concentration of 0.025 w/v %. The surfactants employed are shown in Table 9 below.

The surfactant treatment was conducted under occasional agitation at 28° C. for 6 hours. Of these 2,5-diketo-D-gluconic acid fermentation broths, one treated with SDS was used in the 2-keto-L-gulonic acid fermentation by mutant (II) which will be described later.

TABLE 9

Bacterial effects of various surfactants on the strain (III) FERM-P 5452

| Surfactant (0.025 w/v %) | Decrease in number of viable cells/ml | |
|---|---|---|
| | Initial | After treatment at 28° C. for 6 hours |
| None | $2.3 \times 10^9$ | $1.5 \times 10^8$ |
| Sodium dodecyl sulfate (SDS) | " | $7.5 \times 10^3$ |
| Fatty acid sorbitate (Span 60, available from Kaoo Atlas K.K.) | " | $2.2 \times 10^5$ |
| Sodium stearate | " | $1.7 \times 10^8$ |
| Sodium myristate | " | $1.6 \times 10^8$ |
| Nonion HS 210 | " | $3.8 \times 10^4$ |

TABLE 9-continued

Bacterial effects of various surfactants on the strain (III) FERM-P 5452

| Surfactant (0.025 w/v %) | | Decrease in number of viable cells/ml | |
|---|---|---|---|
| | | Initial | After treatment at 28° C. for 6 hours |
| (available from Nihon yushi K.K. | HS 215 | " | $4.5 \times 10^4$ |
| | HS 230 | " | $6.7 \times 10^4$ |
| | L 4 | " | $2.1 \times 10^5$ |
| | NS 240 | " | $5.0 \times 10^5$ | toring the elimination in the amount of 2,5-diketo-D-gluconic acid in the culture to give its concentration of about 0.2% just after each feeding.

The feeding of the substrate solution was terminated at the 45th hour but the cultivation was continued for further 3 hours to make the total cultivation time after the beginning of the feeding 48 hours.

The fermentation broth was aseptically sampled at predetermined intervals to be analyzed for 2,5-diketo-D-gluconic acid and 2-keto-L-gulonic acid, and viable cells in the sample were counted (Measurement (3)).

The results of the analysis and the measurements are summarized in Table 10.

TABLE 10

| Time after the beginning of 25DKG* fermentation broth feeding (hours) | | Bactericidal treatment of 25DKG fermentation broth | | |
|---|---|---|---|---|
| | | Untreated | Treatment with SDS | Sterilization by filtration |
| 8 | 2KLG**, produced (mg/ml) | 10.2 | 10.8 | 10.9 |
| | Number of viable cells of the strain (III)(cells/ml) | $8.9 \times 10^3$ | Not detected | Not detected |
| 24 | 2KLG, produced (mg/ml) | 14.8 | 18.6 | 18.7 |
| | Number of viable cells of the strain (III)(cells/ml) | $2.3 \times 10^5$ | $3.5 \times 10^3$ | Not detected |
| 48 | 2KLG, produced (mg/ml) | 15.8 | 26.6 | 26.3 |
| | Number of viable cells of the strain (III)(cells/ml) | $3.1 \times 10^7$ | $3.3 \times 10^4$ | Not detected |

*25DKG: 2,5-diketo-D-gluconic acid
*2KLG: 2-keto-L-gulonic acid (1) Addition of D-glucose to the 2,5-diketo-D-gluconic acid fermentation broth An aqueous D-glucose solution (50%) was added to each of the SDS treated fermentation broth, the fermentation broth sterilized by filtration and the untreated broth to give its final concentration of 3.8%, individually, just before the feeding of the broth to the cultured broth of the mutant (II). These 2,5-diketo-D-gluconic acid fermentation broths will be referred to as "substrate solution" hereinafter and used as the raw material for 2-keto-L-gulonic acid production.

(2) Production of 2-keto-L-gulonic acid from 2,5-diketo-D-gluconic acid by the mutant (II)

(i) Seed culture

The seed medium, as described in Example 2, (1), was inoculated with one loopful of the mutuant defective in metabolizing 5-keto-D-gluconic acid and substantially incapable of producing 2-keto-D-gluconic acid (II) FERM-BP 108, derived from *Corynebacterium* sp. FERM-P 2770, ATCC No. 31090 and incubated at 28° C. for 20-24 hours with agitation (71 mm in amplitude, 270 r.p.m.).

(ii) Fermentation (a)

The fermentation medium, as described in Example 4, (2), further containing 0.2% of sodium nitrate, was inoculated with each 50 ml of the seed culture solution and incubated at 28° C. for 10-16 hours at an airflow rate of 600N ml/min. and agitation (1740 r.p.m.).

(iii) Fermentation (b)

After D-glucose was consumed and eliminated from the culture of the mutant (II), FERM-BP, 108, each of substrate solutions prepared as described in (1) above was added separately to the culture so that the 2,5-diketo-D-gluconic acid concentration was 0.2%.

Subsequently, the substrate solution was fed to the culture by portions every 15-120 minutes, while monitoring the elimination in the amount of 2,5-diketo-D-gluconic acid in the culture to give its concentration of about 0.2% just after each feeding.

(3) Counting the number of viable cells of the strain (III)

The sampled fermentation broth was diluted with sterilized physiological saline and spread over a glycerol-bouillon agar medium which was then incubated at 28° C. for 24–36 hours. The viable cells on the medium were counted as colonies.

Note: Since the growth rate of the strain (III) is much higher than that of the mutant (II), cells of the strain (III) intermingled with cells of the mutant (II) can discriminately be counted without substantial difficulty.

From the results of the above experiments, the following facts are confirmed. Namely:

(1) Of various surfactants proposed and evaluated as a bactericidal agent for the strain (III) in the 2,5-diketo-D-gluconic acid fermentation broth, SDS (sodium dodecyl sulfate) is the most excellent in the bactericidal effect (See: Table 9).

(2) In the results (See: Table 10) of the 2-keto-L-gulonic acid-producing experiments in which the three kind of substrate solutions prepared under conditions above are employed;

(i) in a fermentation experiment wherein the untreated substrate solution was used, the number of viable cells of the strain (III) reached $10^5$–$10^7$ cells/ml in 24 hours after the beginning of the addition of the substrate solution while the accumulation of 2-keto-L-gulonic acid scarcely increased after 24 hours as compared with the other two experiments.

(ii) in a fermentation experiment wherein the SDS-treated substrate solution was added, the increase in the number of viable cells of the strain (III) was effectively controlled to less than $10^4$ cells/ml even after 48 hours from the beginning of the addition of the substrate solution, and the accumulation of 2-keto-L-gulonic acid reached about 27 mg/ml, (iii) accumulation of 2-keto-L-gulonic acid in that of (ii) is equivalent to that in a fermentation experiment in which the substrate solution sterilized by filtration was added; and (iv) in the last-mentioned fermentation experiment wherein a substrate solution sterilized by filtration is added, no viable cells of the strain (III) were of course detected and the production of 2-keto-L-gulonic acid proceeded without any difficulty.

What is claimed is:

1. In a process for preparing 2-keto-L-gulonic acid from 2,5-diketo-D-gluconic acid in the presence of a living or processed microorganism capable of producing 2-keto-L-gulonic acid, an improvement which comprises use of a mutant (1) substantially defective in metabolizing 5-keto-D-gluconic acid and (2) substantially incapable of producing 2-keto-D-gluconic acid.

2. A process as claimed in claim 1, wherein said mutant belongs to the Coryneform Group of Bacteria.

3. A process as claimed in claim 1, wherein said mutant belongs to the genus Corynebacterium.

4. A process as claimed in claim 1, wherein said mutant is *Corynebacterium* sp. FERM-BP 107.

5. A process as claimed in claim 1, wherein said mutant is *Corynebacterium* sp. FERM-BP 108.

6. A process as claimed in claim 1, wherein said mutant is cultivated in an aqueous nutrient medium to which 2,5-diketo-D-gluconic acid is fed.

7. A process as claimed in claim 6, wherein said 2,5-diketo-D-gluconic acid is prepared by cultivating a 2,5-diketo-D-gluconic acid producing microorganism which belongs to the genus Gluconobacter or Erwinia in a nutrient medium containing D-glucose in the form of fermentation broth.

8. A process as claimed in claim 7, wherein said 2,5-diketo-D-gluconic acid producing microorganism is selected from the group consisting of *Acetomonas albosesamea* ATCC 21998, *Gluconobacter melanogenum* IFO 3293, *Gluconobacter rubisinosus* IFO 3244, *Erwinia citreus* ATCC 31623, *Erwinia punctata* ATCC 31626, *Erwinia punctata* var. ATCC 31264, *Erwinia punctata* var. ATCC 31625, *Erwinia punctata* var. ATCC 31627, *Erwinia terreus* ATCC 31628, *Erwinia terreus* var. ATCC 31629, *Erwinia terreus* var. ATCC 31630 and *Erwinia terreus* var ATCC 31631.

9. A process as claimed in claim 1, wherein the growth of said mutant and the conversion of 2,5-diketo-D-gluconic acid into 2-keto-L-gulonic acid are effected in the presence of a nitrate salt or a hydrogen donor.

10. A process as claimed in claim 9, wherein said nitrate salt is of an alkali metal or an alkaline earth metal.

11. A process as claimed in claim 9, wherein said nitrate salt is sodium nitrate or potassium nitrate.

12. A process as claimed in claim 9, wherein the concentration of said nitrate salt is 0.05–0.5 w/v%.

13. A process as claimed in claim 9, wherein said hydrogen donor is one selected from the group consisting of carbohydrates and polyhydric alcohols.

14. A process as claimed in claim 9, wherein the growth of said mutant and said conversion are effected in the presence of a carbon source selected from the group consisting of glycerol, glucose, fructose, sucrose and molasses.

15. A process as claimed in claim 9, wherein said hydrogen donor is in an amount of 5–50% of the 2,5-diketo-D-gluconic acid.

16. A process as claimed in claim 7, wherein said 2,5-diketo-D-gluconic acid fermentation broth is sterilized with a surfactant before feeding with 2,5-diketo-D-gluconic acid.

17. A process as claimed in claim 16, wherein said surfactant is sodium dodecyl sulfate (SDS).

18. A process as claimed in claim 17, wherein said SDS is added at a concentration of 0.01–0.25 w/v %.

19. A process as claimed in claim 1, wherein said 2-keto-L-gulonic acid producing microorganism is used in the form of a cell suspension.

20. A process as claimed in claim 1, wherein said 2-keto-L-gulonic acid producing microorganism is used in the form of a cell extract.

21. A mutant characterized in that it is substantially defective in metabolizing 5-keto-D-gluconic acid and substantially incapable of producing 2-keto-D-gluconic acid, which has been derived from a parent, a 2-keto-L-gulonic acid producing microorganism which belongs to Coryneform Group of Bacteria.

22. A mutant as claimed in claim 21, characterized in that said parent belongs to the genus Corynebacterium.

23. *Corynebacterium* sp. FERM-BP 107, as claimed in claim 21.

24. *Corynebacterium* sp. FERM-BP 108, as claimed in claim 21.

* * * * *